(12) United States Patent
Elder et al.

(10) Patent No.: US 8,486,684 B2
(45) Date of Patent: Jul. 16, 2013

(54) METHOD FOR INCREASING ASPARAGINASE ACTIVITY IN A SOLUTION

(75) Inventors: Vincent Allen Elder, Carrollton, TX (US); Christopher J. Koh, Southlake, TX (US); James Keith Henson, Richardson, TX (US)

(73) Assignee: Frito-Lay North America, Inc., Plano, TX (US)

( * ) Notice: Subject to any disclaimer, the term of this patent is extended or adjusted under 35 U.S.C. 154(b) by 1273 days.

(21) Appl. No.: 11/838,153

(22) Filed: Aug. 13, 2007

(65) Prior Publication Data
US 2009/0047725 A1 Feb. 19, 2009

(51) Int. Cl.
C12N 9/82 (2006.01)
A23D 9/013 (2006.01)
A23L 1/212 (2006.01)
A23L 1/216 (2006.01)

(52) U.S. Cl.
USPC ............ 435/229; 426/531; 426/615; 426/637

(58) Field of Classification Search
USPC .......................................... 422/149; 435/229
See application file for complete search history.

(56) References Cited

U.S. PATENT DOCUMENTS

| | | |
|---|---|---|
| 1,782,960 A | 11/1930 | Erysin |
| 2,448,152 A | 8/1948 | Patton |
| 2,490,431 A | 12/1949 | Greene |
| 2,498,024 A | 2/1950 | Baxter |
| 2,584,893 A | 2/1951 | Lloyd |
| 2,611,705 A | 9/1952 | Hendel |
| 2,704,257 A | 3/1955 | deSellano |
| 2,744,017 A | 5/1956 | Baldwin |
| 2,759,832 A | 8/1956 | Cording, Jr. |
| 2,762,709 A | 9/1956 | Janis |
| 2,780,552 A | 2/1957 | Willard |
| 2,893,878 A | 7/1959 | Simon |
| 2,905,559 A | 9/1959 | Anderson |
| 2,910,367 A | 10/1959 | Melnick |
| 2,987,401 A | 6/1961 | Johnston |

(Continued)

FOREIGN PATENT DOCUMENTS

| | | |
|---|---|---|
| EP | 113940 A1 | 7/1984 |
| EP | 1419702 A1 | 5/2004 |

(Continued)

OTHER PUBLICATIONS

Distasio, J. and Niederman, R., "Purification and Characterization of L-Asparaginase with Anti-lymphoma Activity from *Vibrio succinogenes*." Nov. 25, 1976, Journal of Biological Chemistry, vol. 251 No. 22, 6929-6933.*

(Continued)

*Primary Examiner* — Blaine Lankford
*Assistant Examiner* — Charles Zoltan Constantine
(74) *Attorney, Agent, or Firm* — James R. Gourley; Celina M. Orr; Carstens & Cahoon, LLP (57) ABSTRACT

A stable asparaginase solution is disclosed. In one aspect, drinking water is treated to reduce the level of chlorine to enhance the residual enzyme activity of asparaginase. The treatment can occur by removing chlorine constituents or by supplying additives that reduces the level of chlorine. Additives can include reducing agents and chlorine scavengers. Removal technologies can include use of activated carbon, ion exchange, and air stripping.

13 Claims, 1 Drawing Sheet

U.S. PATENT DOCUMENTS

| | | | |
|---|---|---|---|
| 3,026,885 A | 3/1962 | Eytinge |
| 3,027,258 A | 3/1962 | Markakis |
| 3,038,810 A | 6/1962 | Akerboom |
| 3,044,880 A | 7/1962 | Bogyo |
| 3,085,020 A | 4/1963 | Backinger |
| 3,219,458 A | 11/1965 | Higby |
| 3,278,311 A | 10/1966 | Brown |
| 3,305,366 A | 2/1967 | Sutton |
| 3,359,123 A | 12/1967 | Katucki |
| 3,365,301 A | 1/1968 | Lipoma |
| 3,369,908 A | 2/1968 | Gonzalez |
| 3,370,627 A | 2/1968 | Willard |
| 3,404,986 A | 10/1968 | Wimmer |
| 3,436,229 A | 4/1969 | Simpson |
| 3,460,162 A | 8/1969 | Sijbring |
| 3,545,979 A | 12/1970 | Ghafoori |
| 3,578,463 A | 5/1971 | Smith |
| 3,608,728 A | 9/1971 | Trimble |
| 3,620,925 A | 11/1971 | Mochizuki |
| 3,627,535 A | 12/1971 | Davidson |
| 3,634,095 A | 1/1972 | Willard |
| 3,652,402 A | 3/1972 | Chibata |
| 3,687,679 A | 8/1972 | Sijbring |
| 3,690,895 A | 9/1972 | Amadon |
| 3,725,087 A | 4/1973 | Miller |
| 3,755,085 A * | 8/1973 | Tivin et al. ............... 435/263 |
| 3,782,973 A | 1/1974 | Pittet |
| 3,812,775 A | 5/1974 | Sijbring |
| 3,849,582 A | 11/1974 | Blagdon |
| 3,851,572 A | 12/1974 | Lazzarini |
| 3,870,809 A | 3/1975 | Green |
| 3,914,436 A | 10/1975 | Nakadai |
| 3,917,866 A | 11/1975 | Purves |
| 3,925,568 A | 12/1975 | Rao |
| 3,987,210 A | 10/1976 | Cremer |
| 3,997,684 A | 12/1976 | Willard |
| 3,998,975 A | 12/1976 | Liepa |
| 4,005,225 A | 1/1977 | Craig |
| 4,073,952 A | 2/1978 | Standing |
| 4,084,008 A | 4/1978 | Yueh |
| 4,122,198 A | 10/1978 | Wisdom |
| 4,124,727 A | 11/1978 | Rockland |
| 4,136,208 A | 1/1979 | Light |
| 4,140,801 A | 2/1979 | Hilton |
| 4,167,137 A | 9/1979 | van Remmen |
| 4,192,773 A | 3/1980 | Yoshikawa |
| 4,199,612 A | 4/1980 | Fragas |
| 4,210,594 A | 7/1980 | Logan |
| 4,251,895 A | 2/1981 | Caridis |
| 4,272,554 A | 6/1981 | Schroeder |
| 4,277,510 A | 7/1981 | Wicklund |
| 4,312,892 A | 1/1982 | Rubio |
| 4,317,742 A | 3/1982 | Yamaji |
| 4,366,749 A | 1/1983 | Caridis |
| 4,394,398 A | 7/1983 | Wilson |
| 4,418,088 A | 11/1983 | Cantenot |
| 4,461,832 A | 7/1984 | Tschang |
| 4,537,786 A | 8/1985 | Bernard |
| 4,555,409 A | 11/1985 | Hart |
| 4,582,927 A | 4/1986 | Fulcher |
| 4,594,260 A | 6/1986 | Vaquerio |
| 4,595,597 A | 6/1986 | Lenchin |
| 4,645,679 A | 2/1987 | Lee |
| 4,673,581 A | 6/1987 | Fulcher |
| 4,706,556 A | 11/1987 | Wallace |
| 4,721,625 A | 1/1988 | Lee |
| 4,749,579 A | 6/1988 | Haydock |
| 4,751,093 A | 6/1988 | Hong |
| 4,756,916 A | 7/1988 | Dreher |
| 4,806,377 A | 2/1989 | Ellis |
| 4,844,930 A | 7/1989 | Mottur |
| 4,844,931 A | 7/1989 | Webb |
| 4,863,750 A | 9/1989 | Pawlak |
| 4,884,780 A | 12/1989 | Ohashi |
| 4,889,733 A | 12/1989 | Willard |
| 4,900,576 A | 2/1990 | Bonnett |
| 4,917,909 A | 4/1990 | Prosise |
| 4,931,296 A | 6/1990 | Shanbhag |
| 4,933,199 A | 6/1990 | Neel |
| 4,937,085 A | 6/1990 | Cherry |
| 4,963,373 A | 10/1990 | Fan |
| 4,966,782 A | 10/1990 | Heidolph |
| 4,971,813 A | 11/1990 | Strobel |
| 4,978,684 A | 12/1990 | Cerami |
| 4,985,269 A | 1/1991 | Irvin |
| 5,002,784 A | 3/1991 | Pare |
| 5,009,903 A | 4/1991 | deFigueiredo |
| 5,035,904 A | 7/1991 | Huang |
| 5,045,335 A | 9/1991 | DeRooij |
| 5,071,661 A | 12/1991 | Stubbs |
| 5,087,467 A | 2/1992 | Schwank |
| 5,126,153 A | 6/1992 | Beck |
| 5,134,263 A | 7/1992 | Smith |
| 5,137,740 A | 8/1992 | Benson |
| 5,166,123 A * | 11/1992 | Agui et al. ............... 502/426 |
| 5,167,975 A | 12/1992 | Tsurumaki |
| 5,171,600 A | 12/1992 | Young |
| 5,176,933 A | 1/1993 | Fulcher |
| 5,196,225 A | 3/1993 | Lush |
| 5,232,721 A | 8/1993 | Polansky |
| 5,279,840 A | 1/1994 | Baisier |
| 5,292,542 A | 3/1994 | Beck |
| 5,298,274 A | 3/1994 | Khalsa |
| 5,356,646 A | 10/1994 | Simic-Glavaski |
| 5,362,511 A | 11/1994 | Villagran |
| 5,368,879 A | 11/1994 | White |
| 5,370,898 A | 12/1994 | Zussman |
| 5,389,389 A | 2/1995 | Beck |
| 5,391,384 A | 2/1995 | Mazza |
| 5,391,385 A | 2/1995 | Seybold |
| 5,393,543 A | 2/1995 | Laufer |
| 5,394,790 A | 3/1995 | Smith |
| 5,441,758 A | 8/1995 | Lewis |
| 5,447,742 A | 9/1995 | Malvido |
| 5,458,903 A | 10/1995 | Colson |
| 5,464,642 A | 11/1995 | Villagran |
| 5,464,643 A | 11/1995 | Lodge |
| 5,505,978 A | 4/1996 | Roy |
| 5,514,387 A | 5/1996 | Zimmerman |
| 5,534,280 A | 7/1996 | Welch |
| 5,554,405 A | 9/1996 | Fazzolare |
| 5,558,886 A | 9/1996 | Martinez-Bustos |
| 5,571,419 A * | 11/1996 | Obata et al. ............... 210/664 |
| 5,580,598 A | 12/1996 | Benson |
| 5,589,213 A | 12/1996 | Desai |
| 5,603,972 A | 2/1997 | McFarland |
| 5,603,973 A | 2/1997 | Benson |
| 5,620,727 A | 4/1997 | Gerrish |
| 5,676,042 A | 10/1997 | Sakuma |
| 5,690,982 A | 11/1997 | Fazzolare |
| 5,695,804 A | 12/1997 | Hnat |
| 5,707,671 A | 1/1998 | Beck |
| 5,747,084 A | 5/1998 | Cochran |
| 5,776,531 A | 7/1998 | Aasman |
| 5,792,499 A | 8/1998 | Atwell |
| 5,846,589 A | 12/1998 | Baker |
| 5,858,429 A | 1/1999 | Wallace |
| 5,858,431 A | 1/1999 | Wiedersatz |
| 5,887,073 A | 3/1999 | Fazzari |
| 5,919,691 A | 7/1999 | Schulein |
| 5,945,146 A | 8/1999 | Twinam |
| 5,947,010 A | 9/1999 | Barry |
| 5,972,367 A | 10/1999 | Inoue |
| 5,972,397 A | 10/1999 | Durance |
| 6,001,409 A | 12/1999 | Gimmler |
| 6,016,096 A | 1/2000 | Barnes |
| 6,025,011 A | 2/2000 | Wilkinson |
| 6,033,707 A | 3/2000 | Lanner |
| 6,039,978 A | 3/2000 | Bangs |
| 6,066,353 A | 5/2000 | Villagran |
| 6,068,872 A | 5/2000 | Hashiguchi |
| 6,068,873 A | 5/2000 | Delrue |
| RE36,785 E | 7/2000 | Colson |
| 6,139,884 A | 10/2000 | Shifferaw |
| 6,159,530 A | 12/2000 | Christiansen |
| 6,207,204 B1 | 3/2001 | Christiansen |
| 6,210,720 B1 | 4/2001 | Leusner |

| | | |
|---|---|---|
| 6,227,421 B1 | 5/2001 | Richard |
| 6,287,672 B1 | 9/2001 | Fields |
| 6,290,999 B1 | 9/2001 | Gerrish |
| 6,299,914 B1 | 10/2001 | Christiansen |
| 6,335,048 B1 | 1/2002 | Swarvar |
| 6,358,544 B1 | 3/2002 | Henry, Jr. |
| 6,383,533 B1 | 5/2002 | Soeda |
| 6,419,965 B1 | 7/2002 | Douaire |
| 6,436,458 B2 | 8/2002 | Kuechle |
| 6,521,871 B1 | 2/2003 | Shelton |
| 6,528,768 B1 | 3/2003 | Simic-Glavaski |
| 6,531,174 B2 | 3/2003 | Barrett et al. |
| 6,558,730 B1 | 5/2003 | Gisaw |
| 6,565,726 B2 * | 5/2003 | Sato .................... 204/524 |
| 6,599,547 B1 | 7/2003 | Villagran |
| 6,602,533 B1 | 8/2003 | Smith |
| 6,607,777 B1 | 8/2003 | Walsh |
| 6,638,554 B1 | 10/2003 | Rubio |
| 6,638,558 B2 | 10/2003 | Brubacher |
| 6,716,462 B2 | 4/2004 | Prosise |
| 6,770,469 B2 | 8/2004 | Yamaguchi |
| 6,778,887 B2 | 8/2004 | Britton |
| 6,828,527 B2 | 12/2004 | Simic-Glavaski |
| 6,872,417 B1 | 3/2005 | Freudenrich |
| 6,896,528 B2 | 5/2005 | Kubota |
| 6,929,812 B2 | 8/2005 | Van Der Doe |
| 6,989,167 B2 | 1/2006 | Howie |
| 7,037,540 B2 | 5/2006 | Elder |
| 7,122,719 B2 | 10/2006 | Hakimi |
| 7,169,417 B2 | 1/2007 | Dibble |
| 7,189,422 B2 | 3/2007 | Howie |
| 7,190,813 B2 | 3/2007 | Daley |
| 7,220,440 B2 | 5/2007 | Dria |
| 7,267,834 B2 | 9/2007 | Elder |
| 7,291,380 B2 | 11/2007 | Nyholm |
| 7,393,550 B2 | 7/2008 | Barry |
| 7,514,113 B2 | 4/2009 | Zyzak |
| 7,524,519 B2 | 4/2009 | Zyzak |
| 7,527,815 B2 | 5/2009 | Teras |
| 7,534,934 B2 | 5/2009 | Rommens |
| 2002/0018838 A1 | 2/2002 | Zimmerman |
| 2002/0025367 A1 | 2/2002 | Koehler |
| 2002/0129713 A1 | 9/2002 | Caridis |
| 2003/0049359 A1 | 3/2003 | Kulkarni |
| 2003/0183092 A1 | 10/2003 | Barber |
| 2003/0219518 A1 | 11/2003 | Li |
| 2004/0086597 A1 | 5/2004 | Awad |
| 2004/0101607 A1 | 5/2004 | Zyzak |
| 2004/0105929 A1 | 6/2004 | Tomoda |
| 2004/0109926 A1 | 6/2004 | Tomoda |
| 2004/0115321 A1 | 6/2004 | Tricoit |
| 2004/0126469 A1 | 7/2004 | Tomoda |
| 2004/0131737 A1 | 7/2004 | Tomoda |
| 2004/0180125 A1 | 9/2004 | Plank |
| 2004/0180129 A1 | 9/2004 | Plank |
| 2004/0197012 A1 | 10/2004 | Bourg |
| 2004/0224066 A1 | 11/2004 | Lindsay |
| 2005/0064084 A1 | 3/2005 | Elder |
| 2005/0068535 A1 | 3/2005 | Bond |
| 2005/0074538 A1 | 4/2005 | Elder |
| 2005/0079254 A1 | 4/2005 | Corrigan |
| 2005/0118322 A1 * | 6/2005 | Elder .................... 426/637 |
| 2005/0152811 A1 | 7/2005 | Taylor |
| 2005/0196504 A1 | 9/2005 | Finley |
| 2005/0202153 A1 * | 9/2005 | Zyzak et al. .......... 426/621 |
| 2006/0019007 A1 | 1/2006 | Baas |
| 2006/0029992 A1 | 2/2006 | Grune |
| 2006/0088633 A1 | 4/2006 | Barber |
| 2006/0110503 A1 | 5/2006 | Bates |
| 2006/0127534 A1 | 6/2006 | Elder |
| 2006/0193964 A1 | 8/2006 | Eckhoff |
| 2006/0210693 A1 | 9/2006 | Oftring |
| 2006/0216376 A1 | 9/2006 | Milici |
| 2006/0216388 A1 | 9/2006 | Christensen |
| 2007/0042080 A1 | 2/2007 | Plomp |
| 2007/0087101 A1 | 4/2007 | Gusek |
| 2007/0141225 A1 | 6/2007 | Elder |
| 2007/0141226 A1 | 6/2007 | Elder |
| 2007/0141227 A1 | 6/2007 | Boudreaux |
| 2007/0148318 A1 | 6/2007 | Rubio |
| 2007/0166439 A1 | 7/2007 | Soe |
| 2007/0178219 A1 * | 8/2007 | Boudreaux et al. ........... 426/637 |
| 2007/0184175 A1 | 8/2007 | Rubio |
| 2007/0196556 A1 | 8/2007 | Van Der Meer |
| 2007/0281062 A1 | 12/2007 | Bourg |
| 2007/0292589 A1 | 12/2007 | Elder |
| 2008/0003340 A1 | 1/2008 | Karwowski |
| 2008/0008780 A1 | 1/2008 | Streekstra |
| 2008/0101657 A1 | 5/2008 | Durkin |
| 2008/0138480 A1 | 6/2008 | Bows |
| 2008/0144880 A1 | 6/2008 | DeLuca |
| 2008/0166450 A1 | 7/2008 | Corrigan |
| 2008/0166452 A1 | 7/2008 | Corrigan |
| 2008/0253648 A1 | 10/2008 | Mulder |
| 2008/0268111 A1 | 10/2008 | Grune |
| 2008/0279994 A1 | 11/2008 | Cantley |
| 2008/0299273 A1 | 12/2008 | Bhaskar |
| 2009/0074915 A1 | 3/2009 | Hendriksen |
| 2009/0098265 A1 | 4/2009 | Kock |
| 2009/0191310 A1 | 7/2009 | Zyzak |
| 2010/0040729 A1 | 2/2010 | Sahagian |
| 2010/0040750 A1 | 2/2010 | Assaad |
| 2010/0051419 A1 | 3/2010 | Desai |
| 2010/0055259 A1 | 3/2010 | Bourg |
| 2010/0062123 A1 | 3/2010 | Anderson |
| 2010/0112177 A1 | 5/2010 | Bourg, Jr. |
| 2010/0143540 A1 | 6/2010 | Bhaskar |
| 2010/0255167 A1 | 10/2010 | Bourg |
| 2011/0050880 A1 | 3/2011 | Bourg, Jr. |

FOREIGN PATENT DOCUMENTS

| | | |
|---|---|---|
| EP | 1419703 A1 | 5/2004 |
| GB | 156905 | 1/1921 |
| GB | 1132296 | 10/1968 |
| GB | 1519049 | 7/1978 |
| GB | 335214 | 9/1980 |
| JP | 68006927 | 9/1965 |
| JP | 70009815 | 10/1966 |
| JP | 62048351 A | 3/1987 |
| JP | 4104753 | 4/1992 |
| JP | 06030782 A * | 2/1994 |
| JP | 06169713 | 6/1994 |
| JP | 2004-313183 | 11/1994 |
| JP | 05123126 | 5/1998 |
| JP | 10136883 | 5/1998 |
| JP | 11056280 | 3/1999 |
| JP | 11178536 | 7/1999 |
| JP | 2004-180563 | 7/2004 |
| JP | 2004-313183 | 11/2004 |
| JP | 2005-278448 | 10/2005 |
| KR | 910006619 B1 | 8/1991 |
| RU | 2078797 | 5/1997 |
| RU | 2140927 | 11/1999 |
| RU | 2216574 | 11/2003 |
| WO | 95/14397 | 6/1995 |
| WO | 96/01572 | 1/1996 |
| WO | 00/04784 | 2/2000 |
| WO | 00/64280 | 11/2000 |
| WO | 01/91581 | 12/2001 |
| WO | 2004/004484 | 1/2004 |
| WO | 2004/026043 | 4/2004 |
| WO | 2004/028276 | 4/2004 |
| WO | 2004/028277 | 4/2004 |
| WO | 2004/028278 | 4/2004 |
| WO | 2004032647 | 4/2004 |
| WO | 2004032648 | 4/2004 |
| WO | WO 2004030468 A2 * | 4/2004 |
| WO | WO 2004032648 A1 * | 4/2004 |
| WO | 2004039174 | 5/2004 |
| WO | 2004040999 | 5/2004 |
| WO | 2004047559 | 6/2004 |
| WO | 2004/060078 | 7/2004 |
| WO | 2004/080205 | 9/2004 |
| WO | 2006128843 | 12/2006 |
| WO | 2007/106996 | 9/2007 |
| WO | 2008061982 | 5/2008 |

OTHER PUBLICATIONS

Caraway, W. "Chlorine in Distilled Water as a Source of Laboratory Error", Clinical Chemistry, vol. 4 Iss 6, 1958 p. 513-518.*

Water Quality Association, "Technical Application Bulletin: Chloramines", Water Quality Association, Lisle IL, Mar. 2005. Contriubtors and Reviewers, Franks J. et al. pp. 1-5.*

Milli-Q Integral Water Purification System Available at www.millipore.com/catalogue/module.do;jsessionid=3515FA0A37ACE3092D16DB55F75F6E55?id=C72876#1, accessed on Aug. 11, 2012.*

Gray et al "Cycle Chemistry pH measurement" Electric Utility Chemistry Workshop, Champaign Illinois May 12-14, 1998.*

Tikkanen "Guidance Manual for the Disposal of Chlorinated Water" IntregraChemical, Renton, Washington, Available online Sep. 30, 2002 at www.vita-d-chlor.com/specs/AWWARFDechlorGuides.htm, pp. 1-23 and added page showing web-search and date available.*

Nielsen, Per Munk "Enzyme Technology for Production of Protein-Based Flavours" Novo Nordisk A/S 1995 (6 pages).

Ou, Shiyi, et al. "Reduction of Acrylamide Formation by Selected Agents in Fried Potato Crisps on Industrial Scale" ScienceDirect, Innovative Food Science and Emerging Technologies 9 (2008) pp. 116-121.

Pedreschi, Franco, et al. "Acrylamide reduction under different pre-treatments in French fries" ScienceDirect Journal of Food Engineering 79 (2007) pp. 1287-1294.

Pedreschi, Franco, et al. "Color development and acrylamide content of pre-dried potato chips" ScienceDirect Journal of Food Engineering 79 (2007) pp. 786-793.

Pedreschi, Franco, et al. "Color kinetics and acrylamide formation in NaCl soaked potato chips" ScienceDirect Journal of Food Engineering 79 (2007) pp. 989-997.

Pedreschi, Franco, et al. "Reduction of Acrylamide Formation in Potato Slices During Frying" Lebensm.-Wiss u.-Technol. 37 (2004) pp. 679-685.

European Commission—Health and Consumer Protection Directorate-General, "Opinion of the Scientific Committee on Food on new findings regarding the presence of acrylamide in food," Jul. 3, 2002, 16 pages.

Rossell, J.B. (ed.) "Frying—Improving Quality" CRC Press, 2001, pp. 198-214 and 306-308.

Rydberg, Per, et al. "Investigations of Factors That Influence the Acrylamide Content of Heated Foodstuffs" J. Agric. Food Chem. 2003, vol. 51, pp. 7012-7018.

Segtnan, Vegard H., et al. "Screening of acrylamide contents in potato crisps using process variable settings and near-infrared spectroscopy" Mol. Nutr. Food Res. vol. 50, 2006, pp. 811-817.

Talburt & Smith (eds.), Potato Processing 4th Ed. 1987, Ch. 12 "Dehydrated Mashing Potatoe—Potatoe Granules," pp. 535-555, AVI book published by Van Nostrand Reinhold Publisher, New York.

Talburt & Smith (eds.), Potato Processing 4th Ed. 1987, "Improving the Color of Potato Chips," pp. 403-405, AVI book published by Van Nostrand Reinhold Publisher, New York.

"Temperature and Heat—Local Materials" Mar. 2003 found at http://web.archive.org/web/20030321105136/http://www.pa.uky.edu/sciworks/xtra/local.htm (3 pages).

U.S. Food and Drug Administration Public Meeting "Assessing Acrylamide in the U.S. Food Supply," Sep. 30, 2002(5 pages).

Viklund, Gunilla A., et al., "Variety and Storage Conditions Affect the Precursor Content and Amount of Acrylamide in Potato Crisps," J. Sci. Food Agric. 2008, vol. 88, pp. 305-312.

Vivanti, Vittorio, et al. "Level of Acrylamide Precursors Asparagine, Fructose, Glucose, and Sucrose in Potatoes Sold at Retail in Italy and in the United States" J. Food Science, vol. 71, Nr. 2, 2006, pp. C81-C85.

Webb, Edwin C., "Enzyme Nomenclature 1992," Academic Press, p. 422.

Williams, J.S.E., "Influence of Variety and Processing Conditions on Acrylamide Levels in Fried Potato Crisps," ScienceDirect Food Chemistry 90 (2005), pp. 875-881.

Wulfsberg, Gary, Inorganic Chemistry book, University Science Books, 2000, p. 289.

Zhang, Yu, et al., "Study on Formation of Acrylamide in Asparagine-Sugar Microwave Heating Systems Using UPLC-MS/MS Analytical Method," ScienceDirect, Food Chemistry 108 (2008), pp. 542-550.

*Zyzak, David, et al.* v. *Elder, Vincent Allen, et al.*, Board of Patent Appeals and Interferences, Judgment-Arbitration-Bd.R. 126(f), Apr. 14, 2008, 2 pages.

Ashoor, S.H. & Zent, J.B., "Maillard Browning of Common Amino Acids and Sugars," (Abstract), Wiley InterScience Journals: J. Food Science, vol. 49, Issue 4, Jul. 1984, 2 pages.

Database WPI Week 199410 Thomson Scientific, London, GB; AN 1994-079302 XP002503378, Feb. 2, 1994.

Database WPI Week 199805 Thomson Scientific, London, GB; AN 1998-042903 XP002503379, Dec. 4, 1996.

NFRI Report, published Jul. 1, 2004, Report on the symposium named "Chemistry and Safety of Acrylamide in Food" held by the Agricultural and Food Chemistry Division of the American Chemical Society held on Mar. 28-31, 2004 in Anaheim, CA, USA, published by the National Food Research Institute (NFRI) of the National Agricultural and Food Research Organization of Japan (NARO), available at http://oasys2.confex.com/acs/227nm/techprogram/D941.HTM.

Summary Report of "2004 Acrylamide in Food Workshop: Update—Scientific Issues, Uncertainties, and Research Strategies," held on Apr. 13-15, 2004 in Chicago, IL, USA, published on Aug. 6, 2004, by the National Food Research Institute (NFRI) of the National Agricultural and Food Research Organization of Japan (NARO), available at http://222.jifsan.umd.edu/docs/acry2004.

Decision of Rejection, Japanese Pat. App. No. 2007-544461 dated Mar. 16, 2010, translated into English (2 pages).

"Kagaku Dai-jiten (Encyclopedia of Chemistry)," edited by Ohki Michinori, et al., 1989, pp. 317, 96, and 1661 (6 pages).

"Shokuhin Tenkabutsu Binran (List of Food Additives)," 1964, p. 249 (2 pages).

Standard Electrode Potentials, http://www.benjamin-mills.com/chemistry/ecells.htm (2 pages), May 6, 2010.

AFSSA, French Food Safety Agency, "Acrylamide: Information Point," Jul. 24, 2002 (11 pages).

Martinez-Bustos, F., "Effect of the components of maize on the quality of masa and tortillas during the traditional nixtamalisation process," Journal of the Science of Food and Agriculture, vol. 81, pp. 1455-1462, Aug. 13, 2001, 8 pages.

Associated Press Washington—"Habrian descubierto el origen de sustancia cancerigena en las papas fritas," Sep. 30, 2002, cited in Colombian Patent Application No. 05.025.955 Sep. 2009 Office Action, translated by Baker & McKenzie letter dated Sep. 30, 2009 (5 pages).

El Pais.com, "Hallada la reaccion quimica que produce la acrilamida en las frituras," Jul. 15, 2009, cited in Colombian Patent Application No. 05.091.265 Sep. 2009 Office Action, translated by Baker & McKenzie letter dated Sep. 29, 2009 (4 pages).

Kirk, Raymond E., et al. "Enciclopedia de Tecnologia Quimica" 1962, pp. 986-998, cited in Colombian Patent Application No. 05.025.955 Sep. 2009 Office Action, translated by Baker & McKenzie letter dated Sep. 30, 2009 (19 pages).

Dobarganes, Carmen, et al., "Interactions between fat and food during deep-frying," Eur. J. Lipid Sci. Tech. 2000, vol. 102, pp. 521-528.

Erickson, Michael D., ed., Book entitled "Deep Frying—Chemistry, Nutrition and Practical Applications," 2d edition, pp. 262, 263, 274, 275, 2006.

Farid, M.M., et al., "The analysis of heat and mass transfer during frying of food using a moving boundary solution procedure," Heat and Mass Transfer, vol. 34, 1998, pp. 69-77.

Fleck, Fiona, "Experts launch action on acrylamide in staple foods," British Medical Journal, Jul. 20, 2002, p. 120.

Lotfi, Ehsan, et al. "A new approach for automatic quality control of fried potatoes using machine learning," Islamic Azad University, Mashad Branch, Ferdowsi University of Mashad, Khorasan Research Center for Technology Development, Mar. 11, 2009, 4 pages.

Pedreschi, Franco, et al. "Acrylamide content and color development in fried potato strips," ScienceDirect Journal of Food Engineering 39 (2006) pp. 40-46.

Research Disclosure 15172, New process for the manufacture of potato-chips from different types of potatoes (not selected), Nov. 1976, 1 page.

Talburt & Smith (eds.), Potato Processing 4th Ed. 1987, "Improving the Color of Potato Chips," pp. 406-413, AVI Book, Published by Van Nostrand Reinhold Company, New York.

Tareke, E., et al., "Acrylamide: A Cooking Carcinogen?" Chem. Res. Toxicol. 2000, vol. 13, pp. 517-522, Published on Web May 27, 2000 (6 pages).

Centre for Molecular and Biomolecular Informatics article "An Amino Acid Bedtime Story" found at http://www.cmbi.kun.nl. gvteach/HAN/alg/infopages/bedtime.html, material from Friedli Enterprises, Gert Vriend, Apr. 18, 2000, 4 pages.

chemhelper.com Home Page for Frostburg State University—Organic Chemistry Help, article "Nucleophilic Addition to Carbonyl Groups" found at http://www.chemhelper.com/nucadd.html, 2000 (3 pages).

Claeys, Wendie L., et al. "Quantifying the formation of carcinogens during food processing: acrylamide," Trends in Food Science & Technology 16 (2005), pp. 181-193.

de Barber, C. Benedito de, et al. "Reversed-Phase High-Performance Liquid Chromatography Analysis of Changes in Free Amino Acids During Wheat Bread Dough Fermentation" Cereal Chemistry, Feb. 26, 1989, vol. 66, No. 4, pp. 283-288.

Dunlop, Patricia C., et al. "Nitrogen Catabolite Repression of Asparaginase II in *Saccharomyces cerevisiae*" J. Bacteriology, Jul. 1980, vol. 143, No. 1, pp. 422-426.

"FAO/WHO Joint Consultation on the Health Implications of Acrylamide in Food" Summary Report, Geneva, Switzerland, Jun. 25-27, 2002, 12 pages.

Friedman, Mendel, et al., "Browning prevention in fresh and dehydrated potatoes by SH-containing amino acids," Food Additives and Contaminants, 1992, vol. 9, No. 5, pp. 499-503.

Friedman, Mendel, "Chemistry, BioChemistry, and Safety of Acrylamide. A Review," J. Agric. Food Chem., Jul. 3, 2003, vol. 51 (16), pp. 4504-4526.

Garayo, Jagoba, et al. "Vacuum frying of potato chips" J. Food Engineering 55 (2002), pp. 181-191.

Gertz, Christian, et al. "Analysis of acrylamide and mechanisms of its formation in deep-fried products" Eur. J. Lipid. Sci. Technol. 104 (2002), pp. 762-771.

Granda, Claudia, et al., "Effect of Raw Potato Composition on Acrylamide Formation in Potato Chips," J. Food Science vol. 70, Nr. 9, 2005, Nov. 16, 2005, pp. E519-E525.

Granda, Claudia, et al. "Kinetics of Acrylamide Formation During Traditional and Vacuum Frying of Potato Chips" J. Food Process Engineering 28 (2005), pp. 478-493.

Granda, C., et al. "Reduction of Acrylamide Formation in Potato Chips by Low-temperature Vacuum Frying", J. Food Science, vol. 69, Nr. 8, 2004, Oct. 7, 2004, pp. E405-E411.

Grivas, Prof. Spiros, et al. "Acrylamide in Food—Mechanisms of Formation and Influencing Factors During Heating of Foods", Report from Swedish Scientific Expert Committee, Apr. 24, 2002 (22 pages).

Harrison, Karl "Amino Acids and Proteins" found at http://www.chem.ox.ac.uk/mom/amino_acids/introduction.html, 1996 (2 pages).

Harrison, Karl "Molecules of the Month" found at http://www.chem.ox.ac.uk/mom/, 1996 (1 page).

Institute of Food Science & Technology (UK) "Acrylamide Information and News" found at http://www.ifst.org/acrylmd.htm Sep. 6, 2002, 5 pages.

Kim, Kyu-Won, et al. "Asparaginase II of *Saccharomyces cerevisiae*" J. Biological Chem. 263 (24), Aug. 25, 1988, pp. 11948-11953.

Low, Mei Yin, et al. "Effect of Citric Acid and Glycine Addition on Acrylamide and Flavor in a Potato Model System" J. Agric. Food Chem. 2006, 54, pp. 5976-5983.

Mottram, Don—The University of Reading, "Acrylamide in Cooked Foods—the Latest Food Scare" 2002 (44 pages).

Mottram, Donald S. "Acrylamide is formed in the Maillard reaction" Nature Magazine, Oct. 3, 2002, found at www.nature.com/nature (1 page).

Murray, Lindsay, "Acrylamide" Center for Clinical Toxicology, Vanderbilt Univ. Med. Ctr., Jul. 1996 found at http://www.inchem.org/documents/pims/chemical/pim652.htm, Jun. 1998 (8 pages).

Neergaard, Lauran "Scientists: Chemical Reaction May Create Carcinogen" Health Zone found at http://www.cjonline.com/stories/093002/hea_carcinogen.shtml, Sep. 30, 2002 (3 pages).

Procter & Gamble Press Release Sep. 27, 2002 "Procter & Gamble Makes Significant Advances on Understanding Acrylamide Formation" found at http://biz.yahoo.com/prnews/020927/clf005_1.html (2 pages).

Raloff, Janet, "Hot Spuds: Golden Path to Acrylamide in Food" Science News Online, Oct. 5, 2002, vol. 162 found at http://www.sciencenews.org/20021005/fob5.asp (3 pages).

Stadler, Richard H., et al. "Acrylamide from Maillard reaction products" Nature Magazine Oct. 3, 2002 found at www.nature.com/nature (2 pages).

Tareke, Eden, et al., "Analysis of Acrylamide, a Carcinogen Formed in Heated Foodstuffs," J. Agric. Food Chem. pages A through I, 2002.

U.S. Dept. of Health and Human Services, Public Health Service, National Toxicology Program, "9th Report on Carcinogens Revised Jan. 2001" found at http://win2000.kreatiweb.it/sanitaweb/web/Biblioteca/carcinogens/rahc/acrylamide.pdf (5 pages).

U.S. Dept. of Health & Human Services, U.S. Food and Drug Adm., Center for Food Safety and Applied Nutrition "Exploratory Data on Acrylamide in Foods" Dec. 4, 2002 found at http://www.mindfully.org/food/acrylamide-foods-fda (9 pages).

Weisshaar, Rudiger, et al. "Formation of Acrylamide in Heated Potato Products—Model Experiments Pointing to Asparagine as Precursor" Pub. Oct. 3 2002, Deutsche Lebensmittel-Rundschau 98 Jahrgang, Heft (4 pages).

Yarnell, Amanda, "Acrylamide Mystery Solved," Chemical & Engineering News, Oct. 4, 2002 found at http://pubs.acs.org/cen/today/oct4.html (3 pages).

Yaylayan, Varoujan A., et al., "Why Asparagine Needs Carbohydrates to Generate Acrylamide," J. Agric. Food Chem. 2003, vol. 51, pp. 1753-1757.

Zyzak David V. et al., "Acrylamide Formation Mechanism in Heated Foods," J. Agric. Food Chem. 2003, vol. 51, pp. 4782-4787.

Note of the Meeting of Experts on Industrial Contaminants in Food (European Commission): Acrylamide Workshop, Oct. 20-21, 2003, Information on Ways to Lower the Levels of Acrylamide Formed in Food, 6 pages.

Robert, Fabien, et al."Acrylamide Formation from Asparagine under Low-Moisture Maillard Reaction Conditions. 1. Physical and Chemical Aspects in Crystalline Model Systems," J. Agric. Food Chem, 2004, 52, 6837-6842, 6 pages.

Food Standards Agency, "Study of Acrylamide in Food," May 17, 2002, 7 pages.

Abstracts of literature search, "Pathway from Asparagine to Acrylamide," 17 pages, 2009.

Alternative Medicine Review "Glutathione, Reduced (GSH)" vol. 6, No. 6, 2001, pp. 601-607.

Amrein, Thomas, "Influence of Thermal Processing Conditions on Acrylamide Generation and Browning in a Potato Model System," J. Agric. Food Chem. 2006, 54, pp. 5910-5916.

Francis, Frederick J., "Encyclopedia of Food Science and Technology," 2nd ed., 2000, pp. 2160-2161.

Associated Press Washington—"Habrian descubierto el origen de sustancia cancerigena en las papas fritas," Sep. 30, 2002, 2 pages.

Becalski, Adam, et al., "Acrylamide in French Fries: Influence of Free Amino Acids and Sugars," (Abstract), J. Agric. Food Chem. 52 (12), May 22, 2004, 1 page.

Brathen, Erland, et al., "Addition of Glycine Reduces the Content of Acrylamide in Cereal and Potato Products," J. Agric. Food Chem. 2005, vol. 53, pp. 3259-3264.

CBC News CBC.CA "Food sector told to cut down on toxins in chips, fries," Sep. 19, 2002, 2 pages.

CBC News CBC.CA "Scientists find route for toxin to form in fried, baked foods," Sep. 30, 2002, 3 pages.

CBC News CBC.CA "Some acrylamide with your fries?" Jan. 14, 2003, 6 pages.

Database WPI Week 199329 Derwent Publications Ltd., London, GB; AN 1993-234163 XP002473734 & SU 1 750 586 A1 (Interbios Res Assoc) Jul. 30, 1992, 1 page.

Becalski, Adam, et al., "Acrylamide in Foods: Occurrence, Sources, and Modeling," J. Agric. Food Chemistry, 2003, vol. 51, pp. 802-808.

de Meulenaer, Bruno, et al., "Comparison of Potato Varieties Between Seasons and Their Potential for Acrylamide Formation," J. Science Food Agric., vol. 88, 2008, pp. 313-318.

de Vleeschouwer, Kristel, et al., "Impact of pH on the Kinetics of Acrylamide Formation/Elimination Reactions in Model Systems," J. Agric. Food Chem. vol. 54, 2006, pp. 7847-7855.

de Wilde, Tineke, et al., "Influence of Fertilization on Acrylamide Formation during Frying of Potatoes Harvested in 2003," J. Agric. Food Chem., 2006, vol. 54, pp. 404-408.

El Pais.com, "Hallada la reaccion quimica que produce la acrilamida en las frituras," Jul. 15, 2009, 1 page.

Hughes B.P. "The amino acid composition of potato protein and of cooked potato" British J. of Nutrition, vol. 12, Issue 02, May 1958, pp. 188-195.

European Food Safety Authority, Report of "Workshop on Acrylamide Formation in Food," Nov. 17, 2003, Brussels, 22 pages.

Food Safety Consultations "Health Implications of Acrylamide in Food" Report of a Joint FAO/WHO Consultation, Geneva, Switzerland, Jun. 25-27, 2002, 38 pages.

Joint FAO/WHO Expert Commission on Food Additives, 64th Meeting, Rome, Feb. 8-17, 2005, 47 pages.

Fan, Xuetong, et al. "Effectiveness of Ionizing Radiation in Reducing Furan and Acrylamide Levels in Foods" J. Agric. Food Chem. 2006, 54, pp. 8266-8270.

Fiselier, K., et al., "Brown potato Croquettes Low in Acrylamide by Coating with Egg/Breadcrumbs," Eur. Food Res. Technol. (2004) 219:111-115.

Fiselier, Katell, et al., "Higher Acrylamide Contents in French Fries Prepared from 'Fresh' Prefabricates," Eur. Food Res. Technol. (2005) 221:376-381.

Mustafa, Arwa, et al. "Factors Influencing Acrylamide Content and Color in Rye Crisp Bread" J. Agric. Food Chem. 2005, 53, pp. 5985-5989.

Abdel-Kader, Zakia M., "Effect of blanching on the diffusion of glucose from potatoes" (Abstract), Wiley InterScience Journals: Nahrung / Food vol. 36, Iss. 1, 1992, 1 page.

Freshfields Bruckhaus Deringer "Acrylamide in food—The approach of regulators across Europe," Feb. 2003 (20 pages).

Friedman, Mendel, et al., "Inhibition of Browning by Sulfur Amino Acids. 1. Heated Amino Acid-Glucose Systems," J. Agric. Food Chem., 1990, 38, pp. 1641-1647.

Friedman, Mendel, "The Impact of the Maillard Reaction on the Nutritional Value of Food Proteins," Ch. 6 from the Maillard Reaction: Consequences for the Chemical and Life Sciences, Ikan, Raphael (ed.), 1996, 24 pages.

Gokmen, Vural, et al., "Acrylamide formation is prevented by divalent cations during the Maillard reaction," Food Chemistry (2006) doi: 10.1016/j.foodchem.2006.08.011, 8 pages.

Harmony House Foods, Inc., http://web.archive.org/web/20050425210612/www.harmonyhousefoods.com/slicedpotato.html, Apr. 25, 2005, 2 pages.

Health Canada Food & Nutrition "Acrylamide and Food" Dec. 1, 2005 (3 pages).

Health Canada Food & Nutrition "Major pathway of formation of acrylamide in foods and possible approaches to mitigation" Mar. 11, 2005 (2 pages).

Health Canada OCAPI Involving You publication, "Acrylamide and Food," vol. 2, No. 1, Autumn 2002, 2 pages.

Heldman, Dennis R., et al. "Principles of Food Processing" book, 1997, p. 193.

Mizukami, Yuzo, et al. "Analysis of Acrylamide in Green Tea by Gas Chromatography—Mass Spectrometry" J. Agric. Food Chem. 2006, 54, pp. 7370-7377.

Igoe, Robert, Dictionary of Food Ingredients, 4th ed., (Aspen Publishers 2001), pp. 24, 35, 43, 109, and 167.

Ishihara, Katsuyuki, et al. "Examination of Conditions inhibiting the Formation of Acrylamide in the Model System of Fried Potato" Biosci. Biotechnol. Biochem., 70(7), 2006, pp. 1616-1621.

Jacobs, Morris B., Ph.D. "The Chemistry and Technology of Food and Food Products" textbook, 1951, pp. 221-226.

Jespersen, Neil "Chemistry" from Barron's College Review Series on Science, 1997, p. 210.

Jung, M.Y. et al. "A Novel Technique for Limitation of Acrylamide Formation in Fried and Baked Corn Chips and in French Fries," J. Food Science vol. 68, No. 4, 2003, pp. 1287-1290.

Kim, Cheong Tae, et al. "Reducing Acrylamide in Fried Snack Products by Adding Amino Acids" J. Food Science vol. 70, Nr. 5, 2005, pp. C354-C358.

Kirk, Raymond E., et al. "Enciclopedia de Tecnologia Quimica" 1962, pp. 986-998.

Kita, Agnieszka, et al. "Effective Ways of Decreasing Acrylamide Content in Potato Crisps During Processing" J. Agric. Food Chem., Oct. 15, 2004, vol. 52, pp. 7011-7016.

Kretovich, V.L. "Plant Biochemistry" book, 1986, pp. 8-11 (English translation).

Martin, Fiona L., et al. "Formation of Strecker Aldehydes and Pyrazines in a Fried Potato Model System" J. Agric. Food Chem. 2001, 49, pp. 3885-3892.

May, N.J., et al. "Acrylamide formation in deep-fried potato products and removal of acrylamide precursors" Food Australia 58 (10) Oct. 2006, pp. 488-493.

Bosset, Dr. Jacques Olivier, et al. "Mitteilungen aus Lebensmitteluntersuchung und Hygiene" Jun. 2002, vol. 93, Offizielles Organ der Schweizerischen Gesellschaft fur Lebensmittel-und Umweltchemie und der Schweizerischen Gesellschaft fur Lebensmittelhygien(79 pages).

Center for Science in the Public Interest article "New Tests Confirm Acrylamide in American Foods," found at http://www.cspinet.org/new/200206251.html, Jun. 25, 2002, 2 pages.

\* cited by examiner

METHOD FOR INCREASING ASPARAGINASE ACTIVITY IN A SOLUTION

BACKGROUND OF THE INVENTION

1. Technical Field

The present invention relates to a method for reducing the amount of asparagine, a precursor of acrylamide, in a food product. More specifically, this invention relates to increasing the stability of the enzyme asparaginase in a solution.

2. Description of Related Art

As discussed in U.S. Pat. No. 7,037,540, acrylamide has been found in thermally-processed foods containing asparagine. The level of acrylamide formed in some food products can be reduced by adding the enzyme asparaginase to the food product prior to cooking the food product.

The addition of acrylamide reducing enzymes such as asparaginase to food products on a commercial scale, as opposed to a batch scale, presents several challenges. For example, the enzyme asparaginase must contact free asparagine to facilitate the hydrolysis of asparagine. As the enzyme is typically supplied in a relatively concentrated form, the enzyme is ideally mixed and diluted in a water-based solution prior to contacting the food product with the enzyme solution. For example, contacting the food product with the enzyme solution can comprise forming a dough and admixing an enzyme solution with the dough.

A known way to quantify the activity of an enzyme is by referring to the enzyme in terms of units. One unit of enzyme activity is defined as the amount of enzyme required as a catalyst to convert one micromole of substrate in one minute. Thus, knowing the relative concentration of a substrate or compound such as asparagine in a food product, and the amount of food product, one can calculate the units of enzyme, such as asparaginase, required to convert the desired chemical compound, in this case, asparagine, into a different chemical compound.

For previously unknown reasons, even when excess doses (meaning more than the mathematically expected amount required to convert all the asparagine in the food product) of the asparaginase enzyme are used in a food product, such as potato mash or corn masa, there oftentimes are still measurable levels of asparagine in the dough. Because it is desired to reduce the level of acrylamide formed when certain foods are thermally processed, it would be desirable to have a system and method of maximizing the effectiveness of an enzyme used to reduce acrylamide pre-cursors in food products made on a commercial scale.

SUMMARY OF THE INVENTION

The present invention, in one aspect, is directed towards a method of making a stable asparaginase solution from drinking water by removing chlorine from the water. In one aspect, chlorine is removed by ion exchange, reverse osmosis, activated carbon, and/or by air stripping. In one aspect, additives such as reducing agents and chlorine scavengers are used to treat the drinking water. The treated water, in one aspect, is then admixed with asparaginase to make an asparaginase solution. The above as well as additional features and advantages of the present invention will become apparent in the following written detailed description.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

In one embodiment, the present invention is directed towards providing a water-based solution that enhances asparaginase stability and preserves asparaginase activity. Enhanced asparaginase activity can translate into more effective acrylamide reduction in food products because asparagine is a pre-cursor of acrylamide. As used herein, the term "enzyme activity" is expressed in units. Each unit of asparaginase can hydrolyze one micromole of asparagine in one minute.

In one embodiment, the food product in which it is desired to reduce the level of acrylamide formed upon thermal processing is formed from a dough. The term "fabricated snack" means a snack food that uses as its starting ingredient something other than the original and unaltered starchy starting material. For example, fabricated snacks include fabricated potato chips that use a dehydrated potato product as a starting material and corn chips that use masa flour as its starting material. It is noted here that the dehydrated potato product can be potato flour, potato flakes, potato granules, or other forms in which dehydrated potatoes exist. When any of these terms are used in this application, it is understood that all of these variations are included. By way of example only, and without limitation, examples of "fabricated foods" to which an asparaginase solution can be added include tortilla chips, corn chips, potato chips made from potato flakes and/or fresh potato mash, multigrain chips, corn puffs, wheat puffs, rice puffs, crackers, breads (such as rye, wheat, oat, potato, white, whole grain, and mixed flours), soft and hard pretzels, pastries, cookies, toast, corn tortillas, flour tortillas, pita bread, croissants, pie crusts, muffins, brownies, cakes, bagels, doughnuts, cereals, extruded snacks, granola products, flours, corn meal, masa, potato flakes, polenta, batter mixes and dough products, refrigerated and frozen doughs, reconstituted foods, processed and frozen foods, breading on meats and vegetables, hash browns, mashed potatoes, crepes, pancakes, waffles, pizza crust, peanut butter, foods containing chopped and processed nuts, jellies, fillings, mashed fruits, mashed vegetables, alcoholic beverages such as beers and ales, cocoa, cocoa powder, chocolate, hot chocolate, cheese, animal foods such as dog and cat kibble, and any other human or animal food products that are subject to sheeting or extruding or that are made from a dough or mixture of ingredients.

The use of the term "fabricated foods" herein includes fabricated snacks as previously defined. The use of the term "food products" herein includes all fabricated snacks and fabricated foods as previously defined.

As referred to herein, the thermally-processed foods include foods that can be treated with an asparaginase solution, by way of example and without limitation, all of the foods previously listed as examples of fabricated snacks and fabricated foods, as well as French fries, sliced potatoes, yam fries, other tuber or root materials, cooked vegetables including cooked asparagus, onions, and tomatoes, coffee beans, cocoa beans, cooked meats, dehydrated fruits and vegetables, heat-processed animal feed, tobacco, tea, roasted or cooked nuts, soybeans, molasses, sauces such as barbecue sauce, plantain chips, apple chips, fried bananas, and other cooked fruits.

According to some such embodiments, the desired ingredients for making the dough are mixed together with water, and the desired amount of asparaginase is also mixed with treated water to make an asparaginase solution. The asparaginase solution can then be added to the dough. In one embodiment, an asparaginase solution is mixed directly with desired ingredients to make a dough. The dough can then be made into a thermally processed food product.

In a commercial facility, the water used to form the dough and the asparaginase solution is that water that is readily available to the facility, which is typically the drinking water supplied to an end-user from the local municipal water supply. As used herein, "drinking water" shall mean the water supplied from a potable water supply, and includes, but is not limited to, water from a municipal water supply. Almost all U.S. municipal water supplies add enough chlorine to drinking water so the drinking water has residual chlorine at the customer's tap. Many municipal water districts add chloramine to drinking water because chloramine is more stable than chlorine. As used herein, chlorine is defined as oxidizing forms of chlorine and includes, but is not limited to chloramine and hypochlorites. Similarly, non-oxidizing forms of the chloride ion, such as provided by hydrochloric acid (HCl) and sodium chloride (NaCl), are excluded from the definition.

The present inventors have discovered that certain characteristics of drinking water, for example, the presence of chlorine, reduces the activity of the asparaginase enzyme to a point where it is not useful in a commercial setting for the production of food. As used herein, "residual enzyme activity" (expressed as a %) refers to the enzyme activity of a control divided by the enzyme activity of a sample, and provides a relative measurement of enzyme activity under various test conditions. The present inventors have also identified methods and systems for mitigating the effect of drinking water on enzyme activity and preserving the residual enzyme activity of asparaginase such that it may be useful in a commercial setting. The following examples are illustrative of the foregoing.

EXAMPLE 1

Four Solutions were formed from aliquots, each aliquot having an initial equal Asparaginase (Novozymes A/S) activity added, and each aliquot, diluted with distilled water or drinking water such that each Solution had a total volume of about 50 ml. The drinking water for Solution Nos. 3 and 4 was drinking water supplied from the North Texas Municipal Water District to Plano, Tex. USA. The water types used in each solution are described in the following Table 1a.

TABLE 1a

Type of water used to make an asparaginase solution.

| Solution No. | Type of Water |
|---|---|
| 1 | distilled water |
| 2 | distilled water |
| 3 | drinking water from the North Texas Municipal Water District to Plano, TX USA |
| 4 | drinking water from the North Texas Municipal Water District to Plano, TX USA mixed with 0.1 N hydrochloric acid added to achieve a pH of 6 |

Each of Solution Nos. 2-4 were heated at about 35° C. for about 40 minutes before measuring enzyme activity, and pH using Solution No. 1 as the control for residual enzyme activity comparison. Solution No. 1 was refrigerated for about 40 minutes at a temperature of about 10° C.

The values measured are shown in Table 1b below:

TABLE 1b

Residual enzyme activity of distilled water and drinking water.

| Solution No. | pH of Solution | Relative Activity |
|---|---|---|
| 1 | 6.93 | 100% |
| 2 | 7.00 | 103% |
| 3 | 8.22 | 38% |
| 4 | 7.55 | 48% |

It should be noted that the test results for the enzyme activity and residual enzyme activity were conducted using the Test Method described at the end of this disclosure. As compared to Solution No. 1 (control), Solution No. 2 did not lose any enzyme activity. Solution No. 3 was slightly alkaline, having a pH of about 8.22, and the asparaginase enzyme lost about 62% of its activity after about 40 minutes at about 35° C. The addition of dilute hydrochloric acid to drinking water (Solution No. 4) lowered the pH to about 7.55, and the asparaginase lost about 52% of its activity after about 40 minutes of being heated at about 35° C. Consequently, it appears that the alkalinity of Solution No. 3 is responsible for some loss of enzyme activity. It is generally recognized that pH has an impact on asparaginase activity and the asparaginase activity is higher when the pH is between about 4 and about 7.

EXAMPLE 2

Four Solutions were formed from aliquots, each aliquot having an initial equal

Asparaginase (Novozymes A/S) activity, and each aliquot, diluted with de-ionized water or drinking water such that each Solution had a total volume of about 50 ml. The water types used in each Solution are described in the following Table 2a:

TABLE 2a

Asparaginase Solutions made from different water supplies.

| Sol. No. | Type of Water |
|---|---|
| 1 | De-ionized water (control) |
| 2 | Drinking water from the North Texas Municipal Water District to Plano, TX USA |
| 3 | Drinking water from supplied to residents of Duncanville, TX USA |
| 4 | Water used in a food manufacturing process in Mexicali, Mexico |

Each of Solution Nos. 2-4 were heated at about 35° C. for about 40 minutes before measuring chlorine levels, water hardness, pH, and enzyme activity. The control was not heated. The measured values are shown in Table 2b below.

TABLE 2b

Residual enzyme activity and water chemistry of three different drinking water solutions.

| Solution No. | Free Chlorine (mg/L) | Total Chlorine (mg/L) | Total Hardness (mg/L) | pH | Activity |
|---|---|---|---|---|---|
| 1 | 0 | 0 | 0 | 6.89 | 100% |
| 2 | 1.0 | 1.0 | 232 | 7.47 | 9% |

TABLE 2b-continued

Residual enzyme activity and water chemistry of three different drinking water solutions.

| Solution No. | Free Chlorine (mg/L) | Total Chlorine (mg/L) | Total Hardness (mg/L) | pH | Activity |
|---|---|---|---|---|---|
| 3 | 0.02 | 0.02 | 90 | 7.87 | 85% |
| 4 | 0.02 | 0.06 | 28 | 8.00 | 89% |

This data clearly demonstrates the negative impact chlorine has on residual enzyme activity. For example, Solution No. 1 (control) had no chlorine and had the highest residual enzyme activity. Solution No. 2 had the lowest level of residual enzyme activity, and the highest level of free chlorine and total hardness.

Solution No. 3 had a relatively low concentration of free chlorine, and a moderate hardness level, with a residual activity of over 80%. Solution No. 4 had a free-chlorine concentration similar to that of Solution No. 3, and a lower hardness level, resulting in a slightly higher residual activity. Table 2b demonstrates that the residual enzyme activity of asparaginase is inversely proportional to the level of chlorine.

EXAMPLE 3

Four Solutions were formed from aliquots, each aliquot having an initial equal Asparaginase (Novozymes A/S) activity, and each aliquot, diluted with de-ionized water or drinking water such that each Solution had a total volume of about 50 ml. The water types for each sample are listed in Table 3a below.

TABLE 3a

Type of chlorinated water used to make an asparaginase solution

| Sol. No. | Type of Water |
|---|---|
| 1 | De-ionized water (control) |
| 2 | De-ionized water + sufficient hypochlorite to yield 12 ppm chlorine |
| 3 | Drinking water from the North Texas Municipal Water District to Plano, TX USA |
| 4 | Drinking water from the North Texas Municipal Water District to Plano, TX USA, filtered through a BRITA filter three times |

Each of Solutions Nos. 2-4 were heated at about 35° C. for 40 minutes before measuring free chlorine, total hardness, pH and residual enzyme activity.

The values measured are shown in Table 3b below:

TABLE 3b

Residual enzyme activity of solutions having various levels of chlorine.

| Solution No. | Free Chlorine (mg/L) | Total Hardness (mg/L) | pH | Activity |
|---|---|---|---|---|
| 1 | 0 | — | 4.81 | 100% |
| 2 | Not Measured | — | 5.87 | 4% |
| 3 | Not Measured | 228 | 7.10 | 21% |
| 4 | 0 | 20 | 4.99 | 102% |

As Table 3b above indicates, the addition of chlorine to deionized water as shown by Solution 2 or chlorine's presence in drinking water as shown by Solution 3 clearly lowers the residual activity of the asparaginase enzyme. Further, the removal, or absence of chlorine, clearly results in an increased activity of enzyme, as demonstrated by the residual activity level of enzyme in deionized water in Solution 1 and as demonstrated by the residual enzyme activity in BRITA filtered water in Solution 4. The chlorine level for Solution 2 was not measured because Chlorine in the form of sodium hypochlorite was added to the solution. Also, because drinking water was being, the relative level of chlorine in Solution 3 was known to mimic drinking water levels.

EXAMPLE 4

The objective of this test was to analyze the effect of chlorine on enzyme activity by adding an amount of chlorine found in drinking water to deionized water having no chlorine to ascertain the effects of chlorine on asparaginase activity.

Four Solutions were formed from aliquots, each aliquot having an initial equal Asparaginase (Novozymes A/S) activity, and each aliquot, diluted with de-ionized water or drinking water such that each Solution had a total volume of about 50 ml. The water types for each sample are listed in Table 4a below.

TABLE 4a

Type of chlorinated water used to make an asparaginase solution

| Solution No. | Type of Water |
|---|---|
| 1 (control) | deionized water |
| 2 | acidified deionized water with sufficient sodium hypochlorite to result in water having 1.2 ppm chlorine and sufficient hydrochloric acid to result in an acidic pH |
| 3 | acidified deionized water with sufficient sodium hypochlorite to result in water having 0.2 ppm chlorine and sufficient hydrochloric acid to result in an acidic pH |
| 4 | Drinking water from the North Texas Municipal Water District to Plano, TX USA |

Each of Solutions Nos. 2-4 were heated at about 35 C for 40 minutes before measuring chlorine, pH and residual enzyme activity. Solution 1 was not heated. The values measured are shown in Table 4b below:

TABLE 4b

Residual enzyme activity of solutions having various levels of chlorine.

| Solution | Free Chlorine (mg/L) | Total Chlorine (mg/L) | pH | Activity |
|---|---|---|---|---|
| 1 | — | — | 4.85 | 100 |
| 2 | 1.2 | 1.2 | 4.69 | 3 |
| 3 | 0.1 | 0.2 | 4.62 | 108 |
| 4 | 0.8 | 1.1 | 6.84 | 14 |

The data in Table 4b above demonstrates that when chlorine alone is added to water, the residual asparaginase activity is substantially lowered. However, at relatively low levels, chlorine has less impact on the residual enzyme activity.

EXAMPLE 5

Five solutions were prepared to ascertain the potential effects of drinking water modification on the residual activity of asparaginase. Each solution was formed from aliquots, each aliquot having an initial equal Asparaginase (Novozymes A/S) activity, and each aliquot, diluted with de-ionized water or drinking water such that each Solution had a total volume of about 50 ml. The citric acid was added to make the solutions slightly acidic. The water types used in each Solution are described in the following Table 5a:

TABLE 5a

Modifications to drinking water

| Solution No. | Type of Water |
|---|---|
| 1 | De-ionized water |
| 2 | Drinking water from the North Texas Municipal Water District to Plano, TX USA |
| 3 | Acidified Drinking water from the North Texas Municipal Water District to Plano, TX USA with sufficient citric acid to have 100 ppm citric acid |
| 4 | Acidified Drinking water from the North Texas Municipal Water District to Plano, TX USA with sufficient citric acid to have 100 ppm citric acid and 950 ppm of EDTA |
| 5 | Acidified Drinking water from the North Texas Municipal Water District to Plano, TX USA with sufficient citric acid to have 100 ppm citric acid and with sufficient thiosulfate to have 10 ppm of sodium thiosulfate |

Each of Solutions Nos. 2-5 were heated at about 35° C. for 40 minutes before measuring free chlorine, total chlorine, pH and residual enzyme activity. Solution 1 was not heated. The values measured are shown in Table 5b below:

TABLE 5b

Residual enzyme activity of various treated drinking water solutions.

| Solution | Free Chlorine (ppm) | Total Chlorine (ppm) | pH | Residual Activity |
|---|---|---|---|---|
| 1 | 0 | 0 | — | 100% |
| 2 | 0.2 | 1.2 | 7.53 | 12% |
| 3 | 0.4 | 0.8 | 5.81 | 32% |
| 4 | 1.0 | 1.0 | 6.45 | 100% |
| 5 | 0.1 | 0.4 | 5.65 | 86% |

Figure 1A:
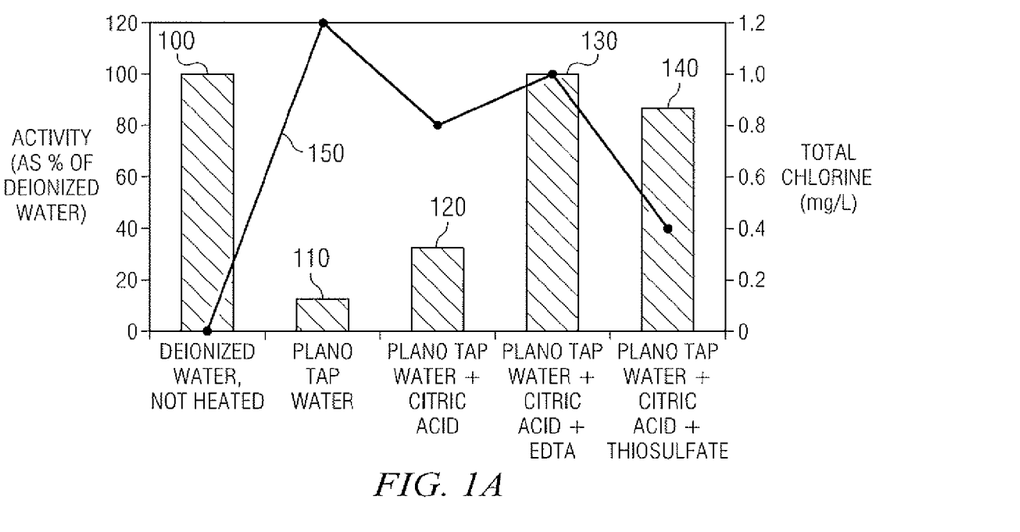
FIG. 1a is a graphical representation of the residual enzyme activity after various treatments of drinking water.

FIG. 1a is a graphical representation of the residual enzyme activity after various treatments of drinking water. The enzyme activity is represented by the bars in the bar chart and the total chlorine concentration is represented by the line (150). As evidenced by the data, thiosulfate (added at a level about 5 times greater than the chlorine concentration in drinking water) decreased the chlorine concentration and increased enzyme activity to 86% (140). The drinking water, having a total chlorine of 1.2 ppm had a relatively low residual activity of only 12% (110). Citric acid decreased the level of chlorine in drinking water and increased the enzyme activity to 32% (120).

Enzyme activity (130) in drinking water with EDTA was equivalent to the enzyme activity of de-ionized water (100), but EDTA only slightly decreased the total chlorine. Without being bound by theory, Applicants believe that the EDTA may either jacket and thereby protect the enzyme from chlorine or believe that EDTA may tie up the chlorine. For example, the chlorine still shows up when tested, but the reaction a reversible reaction between EDTA and chlorine may prevent chlorine from oxidizing or otherwise reacting with asparaginase. Thus, the EDTA appears to inactivate the chlorine. Consequently, in one embodiment, additives can be added that inhibit the chlorine from reducing the activity of asparaginase and/or that inactivate the chlorine.

EXAMPLE 6

Five solutions were prepared to ascertain the potential effects of hard water constituents commonly found in drinking water. Each solution was formed from aliquots, each aliquot having an initial equal Asparaginase (Novozymes A/S) activity, and each aliquot, diluted with de-ionized water or drinking water such that each Solution had a total volume of about 50 ml. Each salt solution had salt added to achieve a salt concentration of 5 mM (5 millimolar), which is roughly double the calcium carbonate concentration found in drinking water from Plano, Tex. For example, referring to Table 3b above, the Total Hardness for Solution No. 3 (Plano Drinking water) is 228 mg/L which corresponds to about 2.28 mM. The various types of salts used in each Solution are described in the following Table 6a:

TABLE 6a

Salts added to de-ionized water.

| Solution No. | Type of Water |
|---|---|
| 1 | De-ionized water |
| 2 | De-ionized Water + Sodium Chloride |
| 3 | De-ionized Water + Calcium Chloride |
| 4 | De-ionized Water + Magnesium Nitrate |
| 5 | De-ionized Water + Sodium Bicarbonate |

Each of Solutions Nos. 2-5 were heated at about 35° C. for 40 minutes before measuring residual enzyme activity. The values measured are shown in Table 6b below:

TABLE 6b

Residual enzyme activity of various salt water mixtures.

| Solution | Activity |
|---|---|
| 1 | 100% |
| 2 | 99% |
| 3 | 101% |
| 4 | 96% |
| 5 | 102% |

Figure 1B:
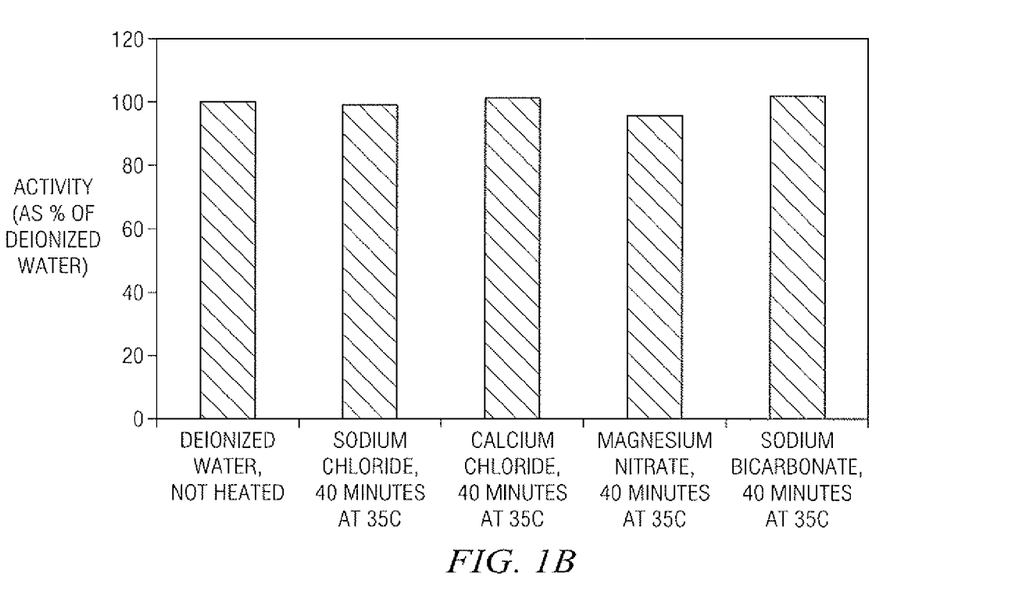
FIG. 1b is a graphical representation of the residual enzyme activity of various salt water mixtures.

FIG. 1b is a graphical representation of the residual enzyme activity of various salt water mixtures and graphically shows the results from Table 6b above. The added salt had no apparent effect on the enzyme stability. Consequently, it is believed that chlorine is responsible for most of loss of asparaginase activity.

EXAMPLE 7

Two aliquots having an initial equal Asparaginase Activity were diluted equally with deionized water (Cell 1) and tap water (Cell 2) to make a first asparaginase solution and a second asparaginase solution. Each solution was held for 30 minutes at room temperature and then each asparaginase solution was then added to corn masa. Asparagine in the masa was measured 5 minutes and 10 minutes after the enzyme was added to the masa and the values measured are shown in Table 7 below.

TABLE 7

Asparagine level in corn masa using enzyme mixed with drinking water and deionized water.

| Type of Water Used for Enzyme Dilution | Masa Sample | Asparagine (ppm) |
|---|---|---|
| Deionized water | 5 minutes after first asparaginase solution added | 3.6 |
| Deionized water | 10 minutes after first asparaginase solution added | 2.9 |

TABLE 7-continued

Asparagine level in corn masa using enzyme mixed with drinking water and deionized water.

| Type of Water Used for Enzyme Dilution | Masa Sample | Asparagine (ppm) |
|---|---|---|
| Drinking water from the North Texas Municipal Water District to Plano, TX USA | 5 minutes after second asparaginase solution added | 37.2 |
| Drinking water from the North Texas Municipal Water District to Plano, TX USA | 10 minutes after second asparaginase solution added | 24.2 |

The level of asparagine in the corn masa shown in Table 7 above, demonstrates that the resultant level of asparagine is highly dependent on the underlying diluted asparaginase solution. In the embodiment shown above, the level difference was on the order of about one magnitude in the level of asparagine in corn masa following treatment by de-ionized water versus drinking water.

The data shown above clearly indicates that the active chlorine level must be lowered to maximize the residual activity of asparaginase. Because the de-ionized water and distilled water are expensive, the present invention provides a way to maximize residual enzyme activity by selectively removing and/or inactivating chlorine from drinking water or other water source.

Any method known in the art that can reduce the concentration of enzyme activity reducing components in drinking water can be used, including but not limited to, treating drinking water to reduce the concentration of the activity reducing component by filtration of drinking water through activated carbon, an air stripper (to volatilize the chlorine), reverse osmosis systems, and/or ion-exchange resins. Drinking water can also be treated by mixing drinking water with deionized water or distilled water in sufficient amounts to lower the concentration of activity reducing components to make a stable enzyme solution.

As used herein, a "scavenger" is any additive that preserves enzyme activity by reacting with chlorine. Consequently, scavengers for enzyme reducing components can be added to the drinking water. For example, in one embodiment, thiosulfate, a scavenger for chlorine is added to the drinking water. Further, other additives can be used to inactivate the chlorine. For example, because chlorine is a strong oxidization agent, reducing agents can also be added to the drinking water to react with the chlorine. Reducing agents are known in oxidation-reduction chemistry to be compounds that are electron donors and oxidizing agents are known to be electron acceptors. Consequently, in one embodiment, one or more reducing agents (e.g., electron donors) can be added to a source of drinking water to inactivate or neutralize the chlorine. Examples of reducing agents include, but are not limited to stannous chloride dihydrate, sodium sulfite, sodium metabisulfite, ascorbic acid, ascorbic acid derivatives, isoascorbic acid (erythorbic acid), salts of ascorbic acid derivatives, iron, zinc, ferrous ions, and combinations thereof.

In one embodiment, the present invention reduces the total chlorine concentration to a level that is between about 0 and less than about 0.5 ppm and preferably between 0 and about 0.1 ppm.

In one embodiment, asparaginase can then be mixed with the treated water to make a stable asparaginase solution and the asparaginase solution can then be mixed with food product. In one embodiment, drinking water is sufficiently treated and a stable enzyme or asparaginase solution occurs when the residual enzyme activity is at least about 80% and more preferably at least about 90% for at least 30 minutes and more preferably for at least about 4 hours after the enzyme has been added to treated drinking water. In one embodiment, the residual enzyme activity is at least about 90% for the time required to get an asparaginase solution admixed into a dough.

Armed this disclosure, one skilled in the art, will be able to ascertain and provide the necessary water compositions to result in the desired residual enzyme activity.

Food products the asparaginase solution can be added to include, but are not limited to, doughs, slurries, and any other consumable products where it is desired to lower the level of acrylamide. For example, in one embodiment, the asparaginase solution is added to a potato slurry made from potato flakes. In one embodiment, the potato slurry is made by adding the asparaginase solution to potato flakes. In one embodiment, the asparaginase solution is used for added water and is added to a flour composition to make a dough. In one embodiment, the asparaginase solution is added to corn masa.

In one embodiment, the present invention comprises a system for providing a stable solution of asparaginase that can be added to a food ingredient having asparagine. In one embodiment, the system comprises a treatment system to treat water. The treatment system can remove components such as chlorine through an activated carbon or with other removal methods listed above and/or the treatment system can provide additives including, but not limited to, reducing agents, chlorine scavengers, or EDTA that enhances the activity of asparaginase to a level that is higher than if the additive had not been added. The treated water can then be routed to a mix tank where asparaginase can be diluted therein to make a stable asparaginase solution. The asparaginase solution can then be metered in or otherwise added to a dough used to make a fabricated food, or thermally processed as described above. The dough can then be further processed (e.g., formed by extrusion and sheeting and thermally processed) as well known in the art. Those skilled in the art, armed with this disclosure will understand that the present invention can be used anywhere an asparaginase solution is desired to reduce the level of acrylamide in a food product.

In one embodiment, the invention comprises a system comprising a source of drinking water and a source of asparaginase, a treatment system operable to enhance the activity of asparaginase in the treated water to a level that is higher than if the treatment had not been occurred, and a delivery system operable to mix the treated drinking water and asparaginase. In one embodiment, the delivery system comprises a mix tank that receives treated water form the treatment system and asparaginase.

The Test Method for used to determine asparaginase activity for the Examples in this application is shown below:

I. Background The SIGMA procedure for asparaginase activity used a Tris buffer at pH 8.6 (Sigma catalogue A 4887). Because food grade asparaginase has low activity at pH-8.6, the assay was changed to pH 7.0 with MOPS (3-morpholinopropanesulfonic acid).

II. Principle:

$$\text{L-Asparagine} + \text{H}_2\text{O} \xrightarrow{Asparagine} \text{L-Aspartate} + \text{NH}_3$$

III. Conditions: T=37 C, pH=7.0, $A_{436}$, Light path=1 cm

IV. Method: Spectrophotometric Stop Rate Determination

V. Reagents a. 100 mM MOPS sodium salt (3-morpholinopropanesulfonic acid). Weigh out 2.09 g of MOPS (Sigma M5162). Dissolve in about 60 ml of DI water at room temperature. Add sodium hydroxide to adjust pH to 7.0. Make up to 100 ml with DI water. Store in refrigerator when not in use.

b. 189 mM L-Asparagine Solution Weigh out 0.25 g of L-asparagine anhydrous, and dissolve in 10 ml DI water. Store in refrigerator when not in use. After refrigeration, sonicate to dissolve asparagine crystals before using.

c. 6 mM Ammonium Sulfate Standard Solution ((NH4)2SO4 Standard) Weigh out 0.079 of ammonium sulfate on an analytical balance, and record weigh to 0.0001 g. Dissolve and make up to volume with 100 ml with DI water. Store in refrigerator when not in use.

a. 1.5 M Trichloroacetic acid (TCA) Weigh out 2.45 g of trichloroacetic acid. Dissolve and make up to 10 ml with DI water.

b. Ammonia Color Reagent: Test kit for Ammonia Nitrogen High, Nesslerization, LaMotte Code 3642-SC, VWR Cat. No. 34186-914. The reagent # 2 contains mercury.

c. Asparaginase Enzyme Solution: Immediately before use, prepare a solution containing 2.0-4.0 units/ml of asparaginase in room temperature deionized water. If enzyme is frozen, thaw completely in lukewarm water before taking an aliquot for dilution. For typical enzyme concentrations, 0.1 ml of enzyme solution can be diluted to 50 ml.

VI. Procedure:
  a. Set heating block for vials to 37 C.
  b. Use an adjustable micropipette to transfer the following reagents into vials (ml):

| Reagent | Test | Enzyme Blank | Std. 1 | Std. 2 | Std. 3 | Reagent Blank |
|---|---|---|---|---|---|---|
| A (Buffer) | 1.00 | 1.00 | 1.00 | 1.00 | 1.00 | 1.00 |
| B (L-ASN) | 0.10 | 0.10 | — | — | — | — |
| C (Ammonium Std.) | — | — | 0.25 | 0.50 | 1.00 | — |
| DI Water | 0.90 | 0.90 | 0.85 | 0.60 | 0.10 | 1.10 |
| F (Enzyme Solution) | 0.10 | — | — | — | — | — | c. Cap vials, and place in heating block at 37 C. Start agitation of heating block.
  d. Remove vials from heating block after 30 minutes. Decap vials, immediately add TCA reagent, and mix. Then add Reagent F (Enzyme Solution) to Enzyme Blank. For enzyme test solutions, the time between removal of the vials from the heating block and addition of TCA should be as short as possible. After TCA is added, time before ammonia measurement is not critical. For blanks and standards, time between removal from the heating block and addition of TCA is not critical.

| Reagent | Test | Enzyme Blank | Std. 1 | Std. 2 | Std. 3 | Reagent Blank |
|---|---|---|---|---|---|---|
| D (TCA) | 0.10 | 0.10 | 0.10 | 0.10 | 0.10 | 0.10 |
| F (Enzyme Solution) | — | 0.10 | — | — | — | — | e. Pipet 0.20 ml of each solution into test tubes or vials. Add 4.30 ml of deionized water, 4 drops of LaMotte reagent #1, and 0.50 ml of LaMotte #2. Mix solutions and leave at room temperature for 10-20 minutes before reading absorbance at 436 nm in 1 cm cell. Zero the spectrophotometer with DI water.

VII. Calculation of Results
  a. The enzyme activity is calculated from a calibration curve for ammonia (umole/0.2 mL).
  b. Description of Calculation Steps.
    i. Calculation of ammonium sulfate standard solution concentration:

$$mM = (0.0809 \text{ g}) * (1000 \text{ } mM/M) * (2 \text{ NH3}/\text{NH4SO4})/((132.14 \text{ g/mole}) * (0.1 \text{ L}))$$

$$= 12.24 \text{ } mM = \text{mmole/L} = \text{umole/ml}$$

Where 0.0809 g is weight of ammonium sulfate for standard ii. Calculate umole of NH3 in 2.2 ml standards:

umole of NH3 in 2.2 mL=(NH3 umole/mL of standard solution)*(mL of standard)

iii. Calculate umole of NH3/0.2 mL:

umole of NH3/0.2 mL=(umole of NH3 in 2.2 ml)*(0.2 mL)/(2.2 mL)

iv. Calculate regression curve with
      x=A436
      y=NH3 umole/0.2 mL
    v. From calibration curve, umole of NH3/0.2 ml is calculated:

umole of NH3/0.2 mL=(slope)*($A436$)+Intercept vi. The activity of the diluted enzyme solution is calculated with the following formula:

Units/ml enzyme=(umole of NH3 liberated)*(2.20)/(0.2*30*0.1) where 2.20 ml=Volume from Step 1 (Step 1 is enzyme assay solution.)
0.2 ml=Volume of Step 1 used in Step 2 (Step 2 is color development.)
30 minutes=Time of assay in minutes
0.1 ml=Volume of enzyme used
    vii. The dilution factor is 50 mL divided by volume of concentrated enzyme diluted to 50 mL,
    viii. Concentration of enzyme solution before dilution=(units/ml of diluted solution)*(dilution factor)

While the invention has been particularly shown and described with reference to several embodiments, it will be understood by those skilled in the art that various other approaches to the preservation of the residual asparaginase activity in solution may be made without departing from the spirit and scope of this invention.

What is claimed is:

1. A method for increasing asparaginase activity in a food product, said method comprising the steps of:
  a) treating a drinking water from a municipal water supply, wherein said treating reduces the combined chlorine concentration to less than about 0.5 ppm wherein the treatment is selected from the group consisting of adding a reducing agent, adding a chlorine scavenger, air stripping and combinations thereof;

b) admixing asparaginase with said treated water to make an asparaginase solution; and c) adding said asparaginase solution to a food product.

2. The method of claim 1 wherein said treating step a) further comprises filtration of the drinking water through activated carbon.

3. The method of claim 1 wherein said treating step a) further comprises using an ion-exchange resin.

4. The method of claim 1 wherein said treating step a) further comprises using reverse osmosis.

5. The method of claim 1 wherein said treating step a) comprises air stripping.

6. The method of claim 1 wherein said asparaginase solution comprises a residual activity of at least about 80%.

7. The method of claim 1 wherein said treating step a) comprises adding a reducing agent.

8. The method of claim 7 wherein said reducing agent comprises one or more agents selected from stannous chloride dihydrate, sodium sulfite, sodium meta-bisulfite, ascorbic acid, ascorbic acid derivatives, isoascorbic acid (erythorbic acid), salts of ascorbic acid derivatives, iron, zinc, ferrous ions, and combinations thereof.

9. The method of claim 1 wherein said treated water comprises a pH of less than about 8.0.

10. The method of claim 1 wherein said drinking water is treated with an additive sufficient to reduce the final total level of chlorine to a level that is lower than if the additive had not been added.

11. The method of claim 10 wherein said additive comprises thiosulfate.

12. The method of claim 1 wherein said treating step a) comprises adding a chlorine scavenger.

13. The method of claim 1, further comprising adding EDTA to the treated water.

* * * * *